United States Patent [19]
Crause et al.

[11] Patent Number: 5,538,946
[45] Date of Patent: Jul. 23, 1996

[54] HIRUDIN DERIVATIVES WITH DELAYED ACTION

[75] Inventors: Peter Crause, Offenbach; Paul Habermann, Eppstein/Taunus; Martin Kramer, Wiesbaden; Rainer Obermeier, Hattersheim am Main; Klaus Sauber, Bad Soden am Taunus; Dominique Tripier, Eppstein/Taunus, all of Germany

[73] Assignee: Hoechst Aktiengesellschaft, Frankfurt am Main, Germany

[21] Appl. No.: 895,436

[22] Filed: Jun. 5, 1992

Related U.S. Application Data

[63] Continuation of Ser. No. 630,774, Dec. 21, 1990, abandoned, which is a continuation of Ser. No. 360,672, Jun. 2, 1989, abandoned.

[30] Foreign Application Priority Data

Jun. 4, 1988 [DE] Germany .......................... 38 19 079.6

[51] Int. Cl.[6] .............................. A61K 38/00; C07K 3/00; C07K 5/00; C07K 7/00
[52] U.S. Cl. .............................. 514/12; 514/21; 530/324; 530/350; 530/402
[58] Field of Search ............................. 514/12, 21, 54, 514/59; 530/324, 350, 402; 536/1.1, 112

[56] References Cited

U.S. PATENT DOCUMENTS

| | | | |
|---|---|---|---|
| 4,703,039 | 10/1987 | Hawiger et al. | 514/21 |
| 4,791,100 | 12/1988 | Kramer et al. | 514/12 |

FOREIGN PATENT DOCUMENTS

| | | | |
|---|---|---|---|
| 1156217 | 11/1983 | Canada . | |
| 0158986 | 4/1985 | European Pat. Off. | 514/2 |
| 0171024 | 7/1985 | European Pat. Off. | 514/2 |
| 158564 | 10/1985 | European Pat. Off. . | |
| 168342 | 1/1986 | European Pat. Off. . | |
| 0209061 | 7/1986 | European Pat. Off. | 514/2 |
| 193175 | 9/1986 | European Pat. Off. . | |
| 200655 | 11/1986 | European Pat. Off. . | |
| 227938 | 7/1987 | European Pat. Off. . | |
| 86/3261 | 10/1986 | South Africa . | |
| WO85/04418 | 10/1985 | WIPO . | |

OTHER PUBLICATIONS

*The Merck Index*, Eleventh Edition, 1989, Susan Budavari, Editor, pp. THER–11 and THER–28.

Torchilin et al., *Annals of the New York Academy of Sciences*, vol. 501, 1987, pp. 481–486.

Richter et al., *Die Pharmazie*, vol. 44, Jan. 1989, pp. 73–74.

Lehninger. *Biochemistry*. 1970, pp. 266, 272, and 273.

Spinner et al., "Quantitative enzyme–linked immunosorbent assay (ELISA) for hirudin", *Journal of Immunological Methods*, vol. 87 (1986), pp. 79–83.

Veronese et al., "Surface Modification of Proteins, Activation of Monomethoxy–Polyethylene Glycols by Phenylchloroformates and Modification of Ribonuclease and Superoxide Dismutase", *Applied Biochemistry and Biotechnology*, vol. 11, (1985), pp. 141–152.

P. Walsmann et al., "Biochemische und pharmakologische Aspekte des Thrombininhibitors Hirudin", Die Pharmazie, 1981, pp. 653–659.

Daniel Bagdy et al, "Hirudin," Naturally Occurring Protease Inhibitors, vol. 54, pp. 669–678.

John W. Fenton, II et al., "Thrombin Active–Site Regions," Seminars in Thrombosis and Hemostasis, vol. 12, No. 3, 1986, pp. 200–208.

Wallace et al., Biochemistry, vol. 28, pp. 10079–10084 (1989).

*Primary Examiner*—Christina Y. Chan
*Assistant Examiner*—A. M. Davenport
*Attorney, Agent, or Firm*—Finnegan, Henderson, Farabow, Garrett & Dunner

[57] ABSTRACT

The present invention relates to hirudin derivatives which are formed from hirudin or the physiologically acceptable salt thereof and a carrier, to a process for the preparation thereof, and to the use thereof as thrombin inhibitor.

10 Claims, No Drawings

HIRUDIN DERIVATIVES WITH DELAYED ACTION

This application is a continuation, of application Ser. No. 07/630,774, filed Dec. 21, 1990, now abandoned, which is a continuation of application Ser. No. 07/360,672, filed Jun. 2, 1989, abandoned.

The invention relates to hirudin derivatives which display a delayed action, to a process for the preparation thereof, and to the use thereof.

Hirudins are disclosed in, for example, EP-A 142,860, EP-A 158,564, EP-A 158,986, EP-A 168,342, EP-A 171,024, EP-A 193,175, EP-A 200,655, EP-A 209,061, EP-A 227,938, DE 3,445,517 A1, DE 3,805,540.6 and Chang, FEBS, vol. 164 (1983) 307. Chang showed, inter alia, that C-terminal shortenings greatly impair the antithrombotic action of hirudin. The importance of hirudins for anticoagulant therapy has also been adeqately described (for example P. Walsmann and F. Markwardt; Pharmazie, 36 (1981) 653). Thus, it specifically inhibits thrombin but is otherwise pharmacologically inert, i.e. no undesired side effects have hitherto been detected.

However, the relatively short retention time of the hirudins in the animal or human body (Richter et al., Haematol. 115 (1988) 64; Markwardt et al., Pharmazie 43 (1988) 202) may be regarded as disadvantageous for medical use as a thrombosis prophylactic.

Hence the invention had the object of finding new hirudin derivatives which have a longer half-life or whose elimination is low.

This object is achieved, surprisingly, by hirudin derivatives formed from hirudin or the physiologically acceptable salt thereof and a carrier.

Examples of suitable hirudins are the compounds described in the references cited on page 1, especially the compounds described in EP-A 171,024, EP-A 158,986, EP-A 209,061 and DE 3,805,540.6, such as, for example, Leu-Thr-Tyr-Thr-Asp-Cys-Thr-Glu-Ser-Gly-Gln-Asn-Leu-Cys-Leu-Cys-Glu-Gly-Ser-Asn-Val-Cys-Gly-Gln-Gly-Asn-Lys-Cys-Ile-Leu-Gly-Ser-Asp-Gly-Glu- -Lys-Asn-Gln-Cys-Val-Thr-Gly-Glu-Gly-Thr-Pro-Lys-Pro-Gln-Ser-His-Asn-Asp-Gly-Asp-Phe-Glu-Glu-Ile-Pro-Glu-Glu-Tyr-Leu-Gln.

These hirudins can be prepared by methods of peptide chemistry generally known to those skilled in the art, see, for example, Houben-Weyl, Methoden der organischen Chemie (Methods of Organic Chemistry), volume 15/2, preferably by means of solid-phase synthesis as described, for example, by B. Merrifield, J. Am. Chem. Soc. 85, 2149 (1963) or R. C. Sheppard, Int. J. Peptide Protein Res. 21, 118 (1983) or by equivalent known methods. Alternatively, the said hirudins can also be obtained by methods of genetic manipulation known to those skilled in the art.

Additionally suitable are the following hirudins modified by genetic engineering methods. Advantageously those where, for example, two of the three lysines naturally occurring in the sequence have been replaced by a natural amino acid, preferably Arg or Asn. Furthermore also those hirudins which have been modified by specific N-(preferably Lys) or C-terminal (preferably Met) extension. In the case of an N-terminal extension, the lysines occurring during the course of the sequence are replaced by another natural amino acid, preferably Asn or Arg. Suitable hirudin derivatives of the present invention are those in which Lys 26 and Lys 35 or Lys 35 and Lys 46 or Lys 26 and Lys 46 in the hirudin have in each case been replaced by a different natural amino acid. Other suitable hirudin derivatives are those in which there has been replacement in the hirudin of Lys 26 by Asn and Lys 35 or Lys 46 by Arg. Still other hirudin derivatives according to the present invention are those in which the hirudin is N-terminal extended by one natural amino acid, and Lys 26, Lys 35 and Lys 46 are replaced by one other natural amino acid. Used as carriers are soluble carriers, especially polysaccharides such as, for example, dextrans (MW 20000–75000 dt), preferably dextrans (MW 70000 dt), levans, heparins (MW 6000–20000 dt) or low molecular weight heparins (MW<6000 dt), polyethylene glycols (MW 1500–15000 dt) or gelatin partial hydrolysates, for example gelatin partial hydrolysates crosslinked with diisocyanates (polygeline, ®Haemaccel), or insoluble carriers such as, for example, Sepharoses, for example CH-Sepharose 4B (from Pharmacia), agaroses, cellulose, hydroxymethacrylates, all of which have been activated by known processes, but especially dextrans, heparins and low molecular weight heparins.

The ratio of hirudin to carrier in the hirudin derivatives can vary greatly. It depends on the nature of the carrier and the reaction conditions.

The invention also relates to a process for the preparation of the hirudin derivatives, which comprises hirudins being reacted with an active carrier at a temperature of 0° C. to 25° C., preferably at 4° C.

The hirudin derivatives according to the invention are valuable thrombin inhibitors which are especially distinguished by an extended half-life, which in turn makes wide-ranging use possible, for example in thrombosis prophylaxis.

Thus, the hirudins and hirudin derivatives are, for example, advantageously used for the surface-coating of heart valves (for example made of plastic), artificial vessels, catheters of biocompatible medical equipment or of filters, membranes and materials such as, for example, ceramics, or customary hemodialysis apparatus. The problem which arises in the determination and the detection of relevant blood components is that the blood which is to be investigated must be pretreated. This may entail problems for the validity of such tests. Tests tubes coated with hirudin open up new possibilities to the practitioner.

Furthermore, hirudins and hirudin derivatives have applications in implants which are used, inter alia, also for delayed release of the active substance, for example osmotic minipumps, biodegradable microcapsules, rods and liposome products.

The hirudin derivatives according to the invention show that hirudins can be reacted with high molecular weight carrier materials with, surprisingly, retention of the hirudin activity. The pharmacokinetic behavior of the hirudin is altered in an advantageous manner. If hirudin and dextran-hirudin are injected into rats in a comparison experiment and a thrombin inhibition assay is used to measure the plasma concentration, a thrombin inhibition is measurable after one hour with an amount of dextran-hirudin which is about 10 times lower. Another advantage is, surprisingly, the increase in the half-life. It is 6 to 7 hours for dextran-hirudin whereas it is 1 to 2 hours for hirudin (Markwardt et al. Pharmazie 43 (1988) 202).

The examples which follow, in which the isohirudin ('Leu-Thr-hirudin') described in German Patent Application 3,805,5406 is used, are intended to explain the invention without, however, confining it to these. Those skilled in the art will be aware that all known hirudins can be reacted with a carrier in a manner equivalent to the hirudin employed, as well as the hirudins described on page 2. In this connection, it is possible for the conditions for individual reactions to alter.

EXAMPLE 1

Preparation of hirudin

Hirudin is synthesized, for example, in yeast cells which secrete hirudin as described in German Patent Application P 3,805,540.6 (HOE 88/F 043). Hirudin is subsequently concentrated by HP20 column chromatography (German Patent Application P 3,738,541.0; HOE 87/F 337). Dialysis and subsequent affinity chromatography on thrombin-Sepharose (Walsmann, P.: Pharmazie 36 ( 1981 ) 860–861 ) are followed by final purification by reversed phase HPLC.

However, synthesis is also possible by use of other known methods of genetic manipulation or peptide chemistry.

EXAMPLE 2

Administration of hirudin and subsequent thrombin inhibition assay

Female and male Wistar rats with a body weight of about 300 g are anesthetized with ethylurethane (1.5 g/kg i.p.). 1000 AT-U/kg of a hirudin derivative or authentic 'Leu-Thr-hirudin', which has been dissolved in physiological saline, are administered i.v. to the rats. A catheter is implanted in the carotid of the animals for blood sampling. Blood is taken from the animals and treated with citrate for the determination of anti-thrombin activity. 0.1 ml of the blood treated in this way is mixed with 0.2 ml of Tris/HCl buffer (0.1 mol/1; pH 7.4) and preincubated at 37° C. After addition of 0.1 ml of a thrombin solution (10 NIH-U/ml) the coagulation time is determined using a Schnitger and Gross coagulometer. In parallel with the experiment a calibration plot is constructed using reference plasma, from which the particular plasma hirudin or plasma hirudin derivative concentration is read off.

EXAMPLE 3

Dextran-hirudin The 'coupling' of 'Leu-Thr-hirudin' onto dextran (MW 70000 dt) is effected by the method of Parikh, J. et al. Meth. Enzymol. 34 (1974) 77. For this purpose, the dextran is activated by a treatment with meta-periodate at 4° C. and subsequently dialyzed and freeze-dried. 2 g of activated dextran are then dissolved in 285 ml of 0.1 mol/1 sodium phosphate buffer (pH 8.8) at room temperature, the solution is cooled to 4° C., 20 mg of hirudin are added, and the mixture is incubated at 4° C. for 14 hours. Then 75 ml are removed and freeze-dried. After the low-molecular weight buffer salts have been removed by gel filtration (®Sephadex G-25, 1 cm×100 cm) the solution is again freeze-dried. The reaction occurs between at least one of the three lysines and the activated dextran.

To reduce the Schiff's base which has formed, 75 mg of $NaBH_4$ are added to the 75 ml of incubated solution, and the solution is stirred at 4° C. for 40 minutes and subsequently dialyzed against water at 4° C. for 24 hours (membrane: Servapor Dialysis Tubing; diameter 10mm, from Serra Feinbiochemica GmbH Heidelberg). This is followed by gel filtration on ®Sephadex G-25 and lyophilization. The dextran-hirudin is purified by means of thrombin-Sepharose affinity chromatography in accordance with Example 1. The dextran-hirudin activity is determined using the method of Griesbach et al. (Thromb. Res. 37 (1985) 347–350). This entails measurement of the inhibition of the thrombin-catalyzed cleavage of chromozyme TH. The measured activity on a molar basis corresponds to that of hirudin. The dextran-hirudin purified in this way is administered i.v. to Wistar rats as in Example 2. A detectable concentration is found in the plasma of the rats after 1 hour. This can be described in the comparison experiment only with an approximately 10 times higher dose of hirudin. If the hirudin concentration in the plasma is followed further, it is found that the half-life for elimination of the substance is 6–7 hours. This is a distinct increase compared with hirudins (1–3 hours). The experimental animals used show no adverse effect on their well-being.

EXAMPLE 4

Sepharose-hirudin 8 mg of hirudin are dissolved in 2 ml of 0.1 M $NaHCO_3$ and 0.5M NaCl at pH=8.0. 400 mg of activated CH-Sepharose 4 B (Pharmacia) are swollen in accordance with the manufacturer's instructions. The protein solution is then added to the carrier and left to stand at 23° C. for 1.5 hours. The immobilisate is then filtered off with suction and left to stand in 0.1M TRIS, pH=8.0, for 1 hour to inactivate remaining binding groups. The carrier is subsequently washed in accordance with the manufacturer's instructions.

The protein coupling yield is 5 %. The biological activity is determined in vitro as in Example 2. The Sepharose-hirudin is isolated from the treated plasma, washed with a 1 to 1.5 M NaCl solution and again employed in the inhibition assay. The measured activity is within the limit of error of the first measurement.

We claim:

1. A hirudin derivative comprising a hirudin or a physiologically acceptable salt thereof covalently bonded to a Polysaccharide carrier, wherein the hirudin derivative is a biologically active thrombin inhibitor.

2. A hirudin derivative comprising a hirudin or physiologically acceptable salt thereof covalently bonded to a carrier, wherein the hirudin derivative is a biologically active thrombin inhibitor, and wherein the carrier is a dextran or a heparin.

3. A hirudin derivative as claimed in claim 2, wherein the carrier is low molecular weight heparin.

4. A hirudin derivative comprising a hirudin or physiologically acceptable salt thereof covalently bonded to a carrier, wherein the hirudin derivative is a biologically active thrombin inhibitor, and wherein the hirudin is

```
     0   1                                        10
    Leu—Thr—Tyr—Thr—Asp—Cys—Thr—Glu—Ser—Gly—Gln—Asn—Leu—Cys—
                                  20
    Leu—Cys—Glu—Gly—Ser—Asn—Val—Cys—Gly—Gln—Gly—Asn—Lys—Cys—
          30                                      40
    Ile—Leu—Gly—Ser—Asp—Gly—Glu—Lys—Asn—Gln—Cys—Val—Thr—Gly—
                        50
    Glu—Gly—Thr—Pro—Lys—Pro—Gln—Ser—His—Asn—Asp—Gly—Asp—Phe—
```

-continued

60
Glu—Glu—Ile—Pro—Glu—Glu—Tyr—Leu—Gln.

5. A hirudin derivative comprising a hirudin or physiologically acceptable salt thereof covalently bonded to a carrier, wherein the hirudin derivative is a biologically active thrombin inhibitor, and wherein the Lys 26 and Lys 35 or Lys 35 and Lys 46 or Lys 26 and Lys 46 in the hirudin have in each case been replaced by a different natural amino acid.

6. A hirudin derivative comprising a hirudin or physiologically acceptable salt thereof covalently bonded to a carrier, wherein the hirudin derivative is a biologically active thrombin inhibitor, and wherein there has been replaced in the hirudin of Lys 26 by Asn and Lys 35 or Lys 46 by Arg.

7. A hirudin derivative comprising a hirudin or physiologically acceptable salt thereof covalently bonded to a carrier, wherein the hirudin derivative is a biologically active thrombin inhibitor, and wherein the hirudin is N-terminal extended by one natural amino acid, and Lys 26, Lys 35 and Lys 46 are replaced by one other naturally occurring amino acid.

8. A hirudin derivative comprising a hirudin or physiologically acceptable salt thereof covalently bonded to a carrier, wherein the hirudin derivative is a biologically active thrombin inhibitor, and wherein the hirudin is C-terminal extended by one natural amino acid.

9. A method for the inhibition of thrombin in a subject, which comprises administering an effective amount of a hirudin derivative comprising a hirudin or physiologically acceptable salt thereof covalently bonded to a carrier, wherein the hirudin derivative is a biologically active thrombin inhibitor.

10. A hirudin derivative comprising a hirudin or physiologically acceptable salt thereof covalently bonded to a carrier, wherein the hirudin derivative is a biologically active thrombin inhibitor, and wherein the carrier is a polyethylene glycol (MW 1500–15000 dt) or a gelatin partial hydrolysate.

* * * * *